United States Patent
Yu et al.

(10) Patent No.: US 11,150,210 B2
(45) Date of Patent: Oct. 19, 2021

(54) SYSTEM AND METHOD FOR IDENTIFYING AND CLEANING CONTAMINATION OF AN ELECTROCHEMICAL SENSOR

(71) Applicant: HONEYWELL INTERNATIONAL INC., Morris Plains, NJ (US)

(72) Inventors: Yuzhong Yu, Morris Plains, NJ (US); Ling Liu, Morris Plains, NJ (US); Feng Liang, Morris Plains, NJ (US)

(73) Assignee: Honeywell International Inc., Morris Plains, NJ (US)

( * ) Notice: Subject to any disclaimer, the term of this patent is extended or adjusted under 35 U.S.C. 154(b) by 88 days.

(21) Appl. No.: 16/329,254

(22) PCT Filed: Aug. 31, 2016

(86) PCT No.: PCT/CN2016/097566
§ 371 (c)(1),
(2) Date: Feb. 28, 2019

(87) PCT Pub. No.: WO2018/039984
PCT Pub. Date: Mar. 8, 2018

(65) Prior Publication Data
US 2020/0025706 A1    Jan. 23, 2020

(51) Int. Cl.
*G01N 27/38* (2006.01)
*G01N 27/30* (2006.01)
(Continued)

(52) U.S. Cl.
CPC ........... *G01N 27/301* (2013.01); *G01N 27/38* (2013.01); *G01N 27/403* (2013.01); *G01N 33/0029* (2013.01)

(58) Field of Classification Search
CPC .... G01N 27/301; G01N 27/38; G01N 27/403; G01N 33/0029; G01N 3/62;
(Continued)

(56) References Cited

U.S. PATENT DOCUMENTS

| 4,566,949 | A | 1/1986 | Berger |
|---|---|---|---|
| 4,729,824 | A | 3/1988 | Giner |

(Continued)

FOREIGN PATENT DOCUMENTS

| CN | 103706583 A | 4/2014 |
|---|---|---|
| CN | 104297311 A | 1/2015 |
| GB | 1531761 A | 11/1978 |

OTHER PUBLICATIONS

International Search Report and Written Opinion for Application No. PCT/CN2016/097566, dated Jun. 7, 2017, 8 pages.
(Continued)

*Primary Examiner* — Robert R Raevis
(74) *Attorney, Agent, or Firm* — Alston & Bird LLP (57) ABSTRACT

Methods and systems for identifying contamination of an electrochemical sensor (10) and cleaning the electrochemical sensor (10) are provided. A method may comprise scanning the sensor (10) for the first time using CV to generate a reference set of readings; scanning the sensor (10) for the second time after the sensor (10) has been employed; comparing a second set of readings from the second CV scan to the reference set of readings; when the second set of readings is different from the reference set of readings, determining that the sensor (10) potential has shifted; scanning the sensor (10) for the third time to clean one or more elements of the sensor (10); scanning the sensor (10) for the fourth time; comparing a fourth set of readings from the fourth CV scan to the second set of readings; and determining that the potential of the sensor (10) has shifted due to pollution of the sensor (10), and/or that the sensor (10) can be further cleaned.

18 Claims, 5 Drawing Sheets

(51) Int. Cl.
*G01N 27/403* (2006.01)
*G01N 33/00* (2006.01)

(58) Field of Classification Search
CPC ........... G01N 27/3274; G01N 33/0006; G01N 35/00594; G01N 35/00693; G01N 33/007
USPC .................. 73/1.02, 1.03, 1.06; 702/84, 104; 134/113, 18
See application file for complete search history.

(56) References Cited

U.S. PATENT DOCUMENTS

| | | |
|---|---|---|
| 4,729,827 A | 3/1988 | Giner |
| 4,772,375 A * | 9/1988 | Wullschleger ......... G01N 27/38 134/1 |
| 6,478,950 B1 | 11/2002 | Peat et al. |
| 7,875,164 B2 | 1/2011 | Santoli et al. |
| 9,036,149 B2 | 5/2015 | MacPherson et al. |
| 2003/0033848 A1* | 2/2003 | Peng .................. G01N 27/4163 73/1.06 |
| 2005/0236280 A1 | 10/2005 | Han et al. |
| 2009/0255829 A1 | 10/2009 | Tixier et al. |
| 2011/0048969 A1 | 3/2011 | Lawrence et al. |
| 2012/0132544 A1 | 5/2012 | Lawrence et al. |
| 2014/0069815 A1* | 3/2014 | Newton ............... G01N 23/223 205/81 |

OTHER PUBLICATIONS

Office Action for Chinese Patent Application No. 2016800887730.9 dated Sep. 1, 2020, 18 pages.
Extended European Search Report for Application No. 16914550.5, dated Feb. 12, 2020, 11 pages.
Second Office Action for Chinese Patent Application No. 2016800887730.9 dated May 6, 2021, 7 pages.

* cited by examiner

SYSTEM AND METHOD FOR IDENTIFYING AND CLEANING CONTAMINATION OF AN ELECTROCHEMICAL SENSOR

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Electrochemical sensors traditionally comprise a gas diffusion working electrode, often based on a platinum or graphite/platinum catalyst dispersed on polytetrafluorethylene (PTFE) tape. The target gas is reacted at this electrode while a balancing reaction takes place at the counter electrode. The electrodes are contained within an outer housing which contains a liquid electrolyte, such as sulfuric acid. The gas typically enters the housing through a controlled diffusion access port, which regulates the ingress of target gas into the cell. The gas reacts at the electrode and affects the electrical output of the sensor.

SUMMARY

In an embodiment, a method for identifying contamination of an electrochemical sensor may comprise scanning the electrochemical sensor a first time using cyclic voltammetry (CV) before the electrochemical sensor has been employed; generating a reference set of readings from the first CV scan; scanning the electrochemical sensor a second time, using a similar scan to the first CV scan, after the electrochemical sensor has been employed; comparing a second set of readings from the second CV scan to the reference set of readings; when the second set of readings is different from the reference set of readings, determining that the electrochemical sensor potential has shifted; scanning the electrochemical sensor a third time, at a different rate from the first CV scan, to at least partially clean one or more elements of the electrochemical sensor; scanning the electrochemical sensor a fourth time, using a similar scan to the first CV scan; comparing a fourth set of readings from the fourth CV scan to the second set of readings; and when the fourth set of readings is different from the second set of readings and closer to the reference set of readings, determining that the potential of the electrochemical sensor has shifted due to pollution of the electrochemical sensor.

In an embodiment, an electrochemical sensor may comprise a housing; an electrolyte disposed within the housing; and a plurality of electrodes in contact with the electrolyte within the housing, wherein the plurality of electrodes comprises a working electrode and a counter electrode; a control circuitry configured to scan the electrochemical sensor a first time using CV before the electrochemical sensor has been employed, thereby generating a reference set of readings from the first CV scan; scan the electrochemical sensor a second time, using a similar scan to the first CV scan, after the electrochemical sensor has been employed, wherein a second set of readings from the second CV scan is compared to the reference set of readings; when the second set of readings is different from the reference set of readings, scan the electrochemical sensor a third time, at a different rate from the first CV scan, to at least partially clean one or more elements of the electrochemical sensor; scan the electrochemical sensor a fourth time, using a similar scan to the first CV scan, wherein a fourth set of readings from the fourth CV scan is compared to the second set of readings; and when the fourth set of readings is different from the second set of readings and closer to the reference set of readings, determine that the potential of the electrochemical sensor has shifted due to pollution of the electrochemical sensor.

In an embodiment, a method for identifying contamination of an electrochemical sensor may comprise scanning the electrochemical sensor a first time using CV before the electrochemical sensor has been employed; generating a reference set of readings from the first CV scan; scanning the electrochemical sensor a second time, using a similar scan to the first CV scan, after the electrochemical sensor has been employed; comparing a second set of readings from the second CV scan to the reference set of readings; when the second set of readings is different from the reference set of readings, determining that the electrochemical sensor potential has shifted; scanning the electrochemical sensor a third time, at a different rate from the first CV scan, to at least partially clean one or more elements of the electrochemical sensor; scanning the electrochemical sensor a fourth time, using a similar scan to the first CV scan; comparing a fourth set of readings from the fourth CV scan to the second set of readings; and determining at least one of: that the potential of the electrochemical sensor has shifted due to pollution of the electrochemical sensor, or that the electrochemical sensor can be further cleaned.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Embodiments of the disclosure include systems and methods for assessing contamination of a reference electrode in an electrochemical sensor, as well as for cleaning the reference electrode of the contamination. In some embodiments, the sensor may comprise a portable or mobile sensor.

In an embodiment of an electrochemical sensor, the sensor may comprise two electrode systems, including a working electrode and a counter electrode. When detecting high concentrations of gases, the working electrode may develop a potential drift caused by the polarization of the counter electrode. This potential drift may cause a non-linear pattern to form when the working electrode reacts with the target gases. To account for this effect, a third reference electrode may be added to the sensor, wherein the working electrode potential may be altered relative to the reference electrode. In this way, the sensor may be configured to test for higher gas concentrations, and may provide improved linearity in the output of the sensor.

In three electrode systems, the reference electrode potential is important. For example, when a Platinum (Pt) air electrode is used in a $H_2SO_4$ system, the potential may typically be approximately 1.06 Volts. Typically, a sensor may have a polarization curve to the target gases, and within a certain range near the reference electrode potential, the sensor's sensitivity may comprise a limiting current platform, where the sensitivity may not be significantly affected by the fluctuation of the drift of the reference electrode. However, if the reference electrode drifts out of the limiting current platform of the polarization curve, or if the sensor's platform is very narrow, the potential of the working electrode may drift with the reference electrode, and the response of the working electrode to the target gases may be reduced to a lower or no response.

During the use of the reference electrode, the reference electrode potential may drift because of one or more factors. For example, the environmental temperature and/or humidity may change, and these changes may affect the potential drift of the sensor. In some cases, temperature and/or humidity compensation may be added to the sensor to account for these effects and possibly reduce the effect of reference electrode potential drift.

In another example, gases from the external environment may affect the potential drift. If testing gases or interfering gases are present at high levels in the environment, the working electrode may be overloaded by the gases, and the non-reacting gases will diffuse to the reference electrode and cause the reference electrode potential drift.

In another example, volatile organic compounds (VOC) may be present in the sensor operating environment, such as ethanol, methanol, formaldehyde, etc. Some of these VOC gases may not react at the working electrode, and may then diffuse to the reference electrode. Additionally, some of the VOC gases may react at the working electrode, but may not react completely in the working electrode, and the residue gases will diffuse into the reference electrode causing a potential drift of the reference electrode.

In some work environments where $H_2S$ sensors may be used, workers use liquid soap containing alcohol to wash their hands after work. The sensors used by these workers may be affected by the presence of the alcohol, which may enter the sensor and diffuse to the reference electrode causing reference electrode potential drift and possibly sensor failure. For this example, it may be desired to reduce the effects of alcohol on reference electrode drift.

In yet another example, contamination of the sensor may be caused by one or more materials from the internal components of the sensor. Many materials may be used when assembling and preparing the sensor (e.g., GFA, GFB, housing, electrolyte, epoxy, catalyst, contact wires), and contamination or impurities in these materials can pollute the reference electrode and may cause a reference electrode potential drift.

Embodiments of the disclosure include an electrochemical sensor with three electrodes, including a working electrode, a reference electrode, and a counter electrode, where all three electrodes are electrically connected by an electrolyte. Additionally, embodiments may include a method to clean the reference electrode of contamination which may cause the reference electrode potential drift, where the reference electrode may be cleaned using cyclic voltammetry of the reference electrode (which may be completed while the sensor is being charged for portable instrument). Embodiments of the disclosure may also include a method for determining the source of the reference electrode potential drift, and if the potential drift is caused by contamination to the reference electrode. If it is determined that the reference electrode is contaminated, the reference electrode may be cleaned.

The method for cleaning the contamination from a reference electrode, optionally while the sensor is charging, may include (while the sensor is charging) rapid cleaning of the reference electrode using CV, where the scan rate can be between approximately 0.5 to 5 Volts per second (V/s). Additionally, during the sensor charging time, the reference electrode may be allowed to return back to its normal condition after the cleaning. The reference electrode potential gradually returns back to its normal state.

Additionally, embodiments may include a method to diagnose the reference electrode potential drift caused by contamination (optionally, while the sensor is charging). The reference electrode may be scanned using CV, and the normal reference electrode CV chart may be saved as a reference, where the scan rate can be between approximately 0.5 to 5 Volts per second (V/s). Then, after the sensor has been used in the environment, the reference electrode may be scanned again using CV (with the same set up as before), and the resulting set of readings, which may be graphed, may be analyzed to determine if the reference electrode potential has drifted. This may be completed by observing one or more peaks indicating hydrogen adsorption and/or one or more peaks indicating oxygen reduction.

In some embodiments, if the potential of the reference electrode has drifted, the reference electrode may be rapidly cleaned using CV, where the scan rate can be between approximately 0.5 to 5 Volts per second (V/s).

To further analyze the contamination of the reference electrode, the reference electrode may be scanned again using CV (with the same set up as before), and the resulting set of readings may be analyzed to determine if the reference electrode potential has been returned to (or at least moved closer to) the normal (reference) value that was determined above. If this is the case, the sensor may be diagnosed as polluted or contaminated at the reference electrode. Then, in some embodiments, the reference electrode may be rapidly cleaned using CV and then allowed to return to the normal state. If the resulting set of readings does not indicate that the cleaning CV scan affected the reference electrode potential, i.e. the potential has not been returned to or moved closer to the normal value, it may be determined that the potential drift is not caused by pollution of the reference electrode.

In some embodiments, the rate and/or range of the CV scanning may be adjusted based on the type of reference electrode. For example, a Pt reference electrode may be scanned from approximately −0.8 to 0.8 Volts, and the sensor cyclic voltammetry time can be approximately $\frac{1}{100}$ to $\frac{1}{20}$ of the total charging time for the sensor. For example, the sensor may be used during the work day and charged overnight, so if the sensor total charging time is approximately 16 hours overnight, then the cleaning time may be between approximately 12 minutes to 48 minutes. During the remaining sensor charging time that occurs after the cleaning, the reference electrode may be allowed to return to its normal circuit control to let the sensor reference electrode potential return to its normal state. The cleaning of the sensor may comprise applying the CV on the sensor aging board and/or on the instrument sensor board.

As discussed above, the contaminant on the reference electrode (or other part of the sensor) may comprise a VOC gas and/or a high concentration of test gases or interfering gases. Also, the contamination may also be generated within the sensor, where the pollution can be from the sensor housing, electrolyte, catalyst, epoxy, contact wires, or assembly material for the sensor, for example.

In an embodiment of the method, during the sensor charging, a first CV scan may be completed on the reference electrode to observe the shift of platinum and oxygen (Pt—O) peaks, to determine whether the potential of the reference electrode has shifted from its normal state. If the potential has shifted, cleaning may be completed, as described above. Then the reference electrode may be allowed to return to its normal control circuit, where the reference electrode potential may drift to its normal value.

Figure 1:
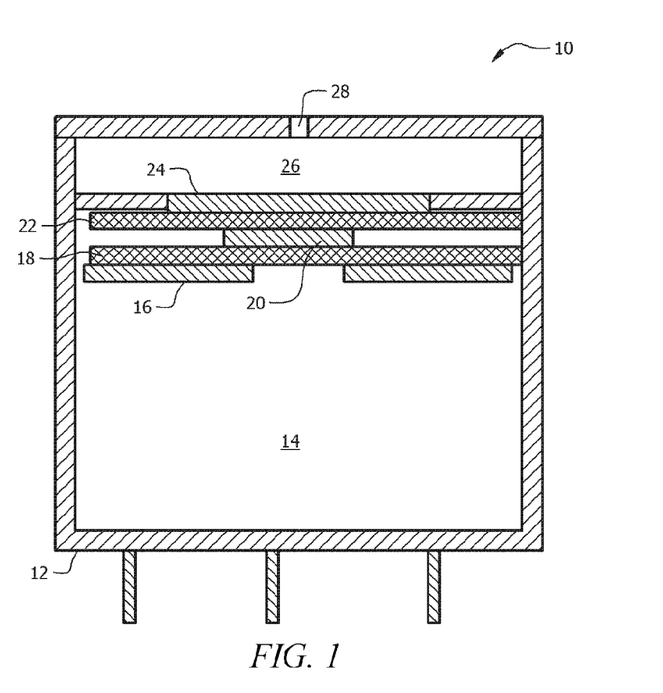
FIG. 1 schematically illustrates a cross section drawing of an electrochemical sensor according to an embodiment.

FIG. 1 is the cross-section drawing of the electrochemical sensor 10. The sensor 10 generally comprises a housing 12 defining a cavity or reservoir 14 designed to hold an electrolyte solution. A working electrode 24 can be placed between an opening 28 and the reservoir 14. A counter electrode 16 and a reference electrode 20 can be positioned within the reservoir. When the gas reacts within the reservoir 14, an electrical current and/or potential can be developed between the electrodes to provide an indication of the concentration of the gas. A reference electrode 20 may also be positioned within the reservoir 14 to provide a reference for the detected current and potential between the working electrode 24 and the counter electrode 16.

The housing 12 defines the interior reservoir 14, and one or more openings 28 can be disposed in the housing to allow a gas to be detected to enter the housing 12 into a gas space 26. The housing 12 can generally be formed from any material that is substantially inert to the electrolyte and gas being measured. In an embodiment, the housing 12 can be formed from a polymeric material, a metal, or a ceramic. For example, the housing can be formed from a material including, but not limited to, acrylonitrile butadiene styrene (ABS), polyphenylene oxide (PPO), polystyrene (PS), polypropylene (PP), polyethylene (PE) (e.g., high density polyethylene (HDPE)), polyphenylene ether (PPE), or any combination or blend thereof.

One or more openings 28 can be formed through the housing 12 to allow the ambient gas to enter the gas space 26 and/or allow any gases generated within the housing to escape. In an embodiment, the electrochemical sensor 10 may comprise at least one inlet opening 28 to allow the ambient gas to enter the housing 12. The opening 28 can be disposed in a cap when a cap is present and/or in a wall of the housing 12. In some embodiments, the opening 28 can comprise a diffusion barrier to restrict the flow of gas (e.g., carbon monoxide, hydrogen sulfide, etc.) to the working electrode 24. The diffusion barrier can be created by forming the opening 28 as a capillary, and/or a film or membrane can be used to control the mass flow rate through the one or more openings 28.

In an embodiment, the opening 28 may serve as a capillary opening to provide a rate limited exchange of the gases between the interior and exterior of the housing 12. In an embodiment, the opening 28 may have a diameter between about 200 μm and about 1.5 mm, where the opening 28 can be formed using a convention drill for larger openings and a laser drill for smaller openings. The opening 28 may have a length between about 0.5 mm and about 5 mm, depending on the thickness of the cap or housing 12. In some embodiments, two or more openings may be present for the inlet gases. When a membrane is used to control the gas flow into and/or out of the housing, the opening diameter may be larger than the sizes listed above as the film can contribute to and/or may be responsible for controlling the flow rate of the gases into and out of the housing 12.

The reservoir comprises the counter electrode 16, the reference electrode 20, and the working electrode 24. In some embodiments, the electrolyte can be contained within the reservoir 14, and the counter electrode 16, the reference electrode 20, and the working electrode 24 can be in electrical contact through the electrolyte. In some embodiments, one or more porous separators 18, 22 or other porous structures can be used to retain the electrolyte in contact with the electrodes. The separators 18, 22 can comprise a porous member that acts as a wick for the retention and transport of the electrolyte between the reservoir and the electrodes while being electrically insulating to prevent shorting due to direct contact between any two electrodes. One or more of the porous separator 18, 22 can extend into the reservoir to provide the electrolyte a path to the electrodes. In an embodiment, a separator 18 can be disposed between the counter electrode 16 and the reference electrode 20, and a separator 22 can be disposed between the reference electrode 20 and the working electrode 24.

One or more of the separators 18, 22 can comprise a nonwoven porous material (e.g., a porous felt member), a woven porous material, a porous polymer (e.g., an open cell foam, a solid porous plastic, etc.), or the like, and is generally chemically inert with respect to the electrolyte and the materials forming the electrodes. In an embodiment, the separators 18, 22 can be formed from various materials that are substantially chemically inert to the electrolyte including, but not limited to, glass (e.g., a glass mat), polymer (plastic discs), ceramics, or the like.

The electrolyte can be any conventional aqueous acidic electrolyte such as sulfuric acid, phosphoric acid, or a neutral ionic solution such as a salt solution (e.g., a lithium salt such as lithium chloride, etc.), or any combination thereof. For example, the electrolyte can comprise sulfuric acid having a molar concentration between about 3 M to about 12 M. Since sulfuric acid is hygroscopic, the concentration can vary from about 10 to about 70 wt % (1 to 11.5 molar) over a relative humidity (RH) range of the environment of about 3 to about 95%. In an embodiment, the electrolyte can comprise phosphoric acid having a concentration in an aqueous solution between about 30% to about 60% $H_3PO_4$ by weight. As another example, the electrolyte can include a lithium chloride salt having about 30% to about 60% LiCl by weight, with the balance being an aqueous solution.

In some embodiments, the electrolyte may be in the form of a solid polymer electrolyte which comprises an ionic exchange membrane. In some embodiments, the electrolyte can be in the form of a free liquid, disposed in a matrix or slurry such as glass fibers (e.g., the separator 18, the separator 22, etc.), or disposed in the form of a semi-solid or solid gel.

The working electrode 24 may be disposed within the housing 12. The gas entering the sensor 10 can contact one side of the working electrode 24 and pass through working electrode 24 to reach the interface between the working electrode 24 and the electrolyte. The gas can then react to generate the current indicative of the gas concentration. As disclosed herein, the working electrode 24 can comprise a plurality of layers. The base or substrate layer can comprise a hydrophobic material or a hydrophobically treated material. A catalytic material can be formed as an electrode on one side of the working electrode 24 and placed in contact with the electrolyte.

In an embodiment, the working electrode 24 can comprise a porous substrate or membrane as the base layer. The substrate can be porous to the gas of interest, which in some embodiments can comprise hydrogen sulfide. In an embodiment, the substrate can comprise a carbon paper formed of carbon or graphite fibers. In some embodiments, the substrate can be made to be electrically conductive through the addition of a conductive material such as carbon. The use of carbon may provide a sufficient degree of electrical conductivity to allow the current generated by the reaction of the gas with the electrolyte at the surface of the working electrode 24 to be detected by a lead coupled to the working electrode 24. Other electrically conductive substrates may also be used such as carbon felts, porous carbon boards, and/or electrically conductive polymers such as polyacetylene, each of which may be made hydrophobic as described below. Alternatively, an electrically conductive lead can be coupled to the catalytic layer to electrically couple the catalytic material to the external circuitry, as described in more detail herein. In an embodiment, the substrate can be between about 5 mils to about 20 mils thick in some embodiments.

The porous substrate can be hydrophobic to prevent the electrolyte from passing through the working electrode 24. The substrate can be formed from a hydrophobic material, or the substrate can be treated with a hydrophobic material. In an embodiment, the substrate can be made hydrophobic through the impregnation of the substrate with a hydrophobic material such as a fluorinated polymer (e.g., PTFE, etc.). In some embodiments, the substrate or membrane can comprise GEFC-IES (e.g., the copolymer of perfluorosulfonic acid and PTFE, which is commercially available from Golden Energy Fuel Cell Co., Ltd.), Nafion® (a copolymer of polytetrafluoroethylene and perfluoro-3,6-dioxa-4-methyl-7-octene-sulfonic acid, which is commercially available from Dupont™), or pure or nearly pure polytetrafluoroethylene (PTFE). The impregnation process can include disposing a hydrophobic material containing solution or slurry on the substrate using a dipping, coating, or rolling process. Alternatively, a dry composition such as a powder can be applied to the substrate. In some embodiments, an optional sintering process can be used to infuse the hydrophobic material into the substrate to create the hydrophobic base layer for the working electrode 24, where both sides of the hydrophobic base layer are hydrophobic. The sintering process can cause the hydrophobic polymer to bond or fuse with the carbon of the substrate to securely bond the hydrophobic material to the substrate.

The resulting substrates can contain about 30% to about 50% by weight of the hydrophobic polymer. The amount of hydrophobic material added to the substrate can affect the electrical conductivity of the substrate, where the electrical conductivity tends to decrease with an increased amount of the hydrophobic material. The amount of the hydrophobic polymer used with the substrate may depend on the degree of hydrophobicity desired, the porosity to the hydrogen sulfide, and the resulting electrical conductivity of the working electrode.

The catalytic layer can be formed by mixing the desired catalyst with a binder and depositing the mixture on the substrate material. The binder can comprise a solution of perfluorinated ion electrolyte solution (e.g., GEFC-IES, Nafion®, etc.), a hydrophobic material such as PTFE, mixtures thereof, or the like. When used as a binder, the GEFC-IES Nafion® and/or PTFE can affect the gas diffusion parameters while supporting the electrocatalyst and maximizing the interfaces between catalyst, gas, and electrolyte at which the electrochemical processes occur. Glycol or other similar chemicals can be used as a diluent to form a catalyst slurry, recipe, or catalyst system, which can be printed on a substrate by a printer.

The catalytic layer might be deposited onto the substrate by, for example, screen printing, filtering in selected areas from a suspension placed onto the substrate, by spray coating, or any other method suitable for producing a patterned deposition of solid material. Deposition might be of a single material or of more than one material sequentially in layers, so as, for example, to vary the properties of the electrode material through its thickness or to add a second layer of increased electrical conductivity above or below the layer which is the main site of gas reaction. Once deposited, the printed element can be sintered at an elevated temperature to form the electrode.

In the working electrode 24, the catalytic layer can comprise carbon (e.g., graphite) and/or one or more metals or metal oxides such as copper, silver, gold, nickel, palladium, platinum, ruthenium, iridium, and/or oxides of these metals. The catalyst used can be a pure metal powder, a metal powder combined with carbon, or a metal powder supported on an electrically conductive medium such as carbon, or a combination of two or more metal powders either as a blend or as an alloy. The materials used for the individual electrodes can be the same or different. In an embodiment, the working electrode 24 comprises a platinum-ruthenium black (Pt—Ru black) electrode. The atomic ratio of the Pt to Ru in the Pt—Ru black can be in the range of about 1:1 to about 1:5, or about 1:2. The catalyst material can have a weight loading per square centimeter ($cm^2$) of the surface area of the working electrode 24 of between about 0.1 $mg/cm^2$ and about 5 $mg/cm^2$, or between about 0.5 $mg/cm^2$ and about 2 $mg/cm^2$, or about 1 $mg/cm^2$.

The counter electrode 16 can be disposed within the housing 12. The counter electrode 16 can comprise a substrate or membrane such as a PTFE membrane, a GEFC-IES membrane, a Nafion® membrane, or the like having a catalytic material disposed thereon. In an embodiment, the catalytic material can be mixed and disposed on the membrane using any suitable process such as rolling, coating, screen printing, or the like to apply the catalytic material on the membrane, as described in more detail herein. The catalyst layer can then be bonded to the membrane through a sintering process as described herein.

In an embodiment, the catalytic material for the counter electrode can comprise a noble metal such as gold (Au), platinum (Pt), ruthenium (Ru), rhodium (Rh), Iridium (Ir), oxides thereof, or any combination thereof. In an embodiment, the catalytic material comprises a Pt—Ru mixture that is screen printed on the membrane, where the membrane can be a GEFC-IES membrane. The catalyst loading for the counter electrode 16 can be within any of the ranges described herein for the working electrode 24. In an embodiment, the catalyst loading for the counter electrode 16 can be the same or substantially the same as the catalyst loading for the working electrode 24, the catalyst loading can also be greater than or less than that of the working electrode 24.

Similarly, the reference electrode 20 can be disposed within the housing 12. The reference electrode 20 can comprise a substrate or membrane such as a PTFE membrane, a GEFC-IES membrane, a Nafion® membrane, or the like having a catalytic material disposed thereon. In an embodiment, the catalytic material can be mixed with a hydrophobic material (e.g., PTFE, etc.) and disposed on the PTFE membrane. Any of the methods used to form the working electrode or the counter electrode can also be used to prepare the reference electrode 20. In an embodiment, the catalytic material used with the reference electrode 20 can comprise a noble metal such as gold (Au), platinum (Pt), ruthenium (Ru), rhodium (Rh), Iridium (Ir), oxides thereof, or any combination thereof. In an embodiment, the catalytic material used to form the reference electrode can comprise a Pt—Ru mixture that is screen printed on the membrane, where the membrane can be a GEFC-IES membrane. The catalyst loading for the reference electrode 20 can be within any of the ranges described herein for the working electrode 24. In an embodiment, the catalyst loading for the reference electrode 20 can be the same or substantially the same as the catalyst loading for the working electrode 24, the catalyst loading can also be greater than or less than that of the working electrode 24. While illustrated in FIG. 1 as having the reference electrode 20, some embodiments of the electrochemical sensor may not include a reference electrode 20.

In order to detect the current and/or potential difference across the electrodes in response to the presence of the hydrogen sulfide, one or more leads or electrical contacts can be electrically coupled to the working electrode 24, the reference electrode 20, and/or the counter electrode 16. The lead contacting the working electrode 24 can contact either side of the working electrode 24 since the substrate comprises an electrically conductive material. In order to avoid the corrosive effects of the electrolyte, the lead contacting the working electrode can contact the side of the working electrode 24 that is not in contact with the electrolyte. Leads may be similarly electrically coupled to the counter electrode 16 and the reference electrode 20. The leads can be electrically coupled to external connection pins to provide an electrical connection to external processing circuitry. The external circuitry can detect the current and/or potential difference between the electrodes and convert the current into a corresponding hydrogen sulfide concentration.

In use, the sensor 10 can detect a hydrogen sulfide concentration. In use, the ambient gas can flow into the sensor 10 through the opening 28, which serves as the intake port for the sensor 10. The ambient gas can comprise hydrogen sulfide. The gas can contact the working electrode and pass through the fine pores of the porous substrate layer to reach the surface of the working electrode 24 treated with the catalyst layer. The electrolyte may be in contact with the surface of the working electrode 24, and the hydrogen sulfide may react and result in an electrolytic current forming between the working electrode 24 and the counter electrode 16 that corresponds to the concentration of the hydrogen sulfide in the ambient gas. By measuring the current, the concentration of hydrogen sulfide can be determined using, for example, the external detection circuitry.

The disclosure having been generally described, the following examples are given as particular embodiments of the disclosure and to demonstrate the practice and advantages thereof. It is understood that the examples are given by way of illustration and are not intended to limit the specification or the claims in any manner.

In an example, an electrochemical $H_2S$ sensor may comprise a capillary hole of approximately 2.6 mm, may comprise a working electrode with PTFE and gold (Au), and may comprise reference and counter electrodes with PTFE and platinum (Pt), where the elements of the sensor may be made using methods as would be known to those skilled in the art. A first CV scan (CV-1) may be completed on the sensor at a rate of approximately 0.1 V/s for four segments from approximately −0.8 to 0.8 V, and the set of readings (which may be graphically illustrated) generated by the scan may be analyzed to identify a Pt—O reduction curve peak.

Figure 2:
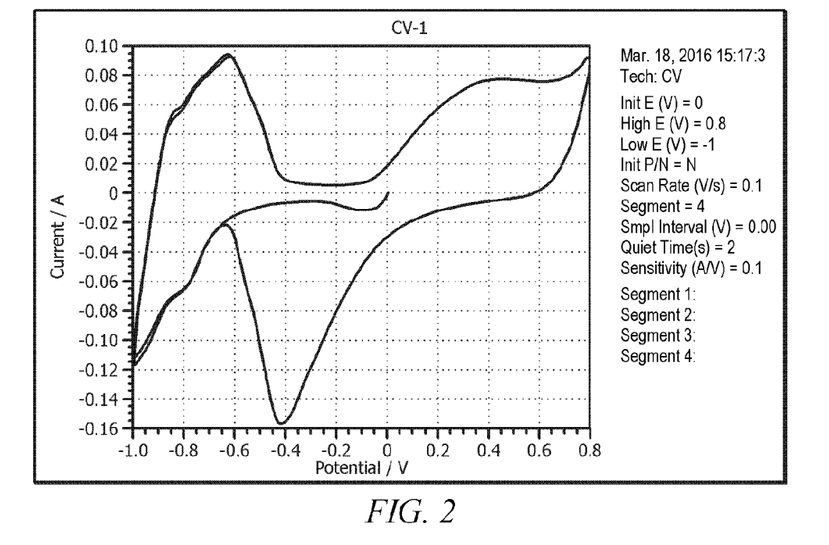
FIG. 2 illustrates a graphical representation of a first set of readings generated by a CV scan of the electrochemical sensor according to an embodiment.

As shown in FIG. 2, the Pt—O reduction curve peak may be located at approximately −0.4 V. Then the sensor may be placed on a sensor aging board for approximately 24 hours. After aging, the sensor may be purged with approximately 5000 ppm ethanol balance with air for approximately 40 minutes.

Figure 3:
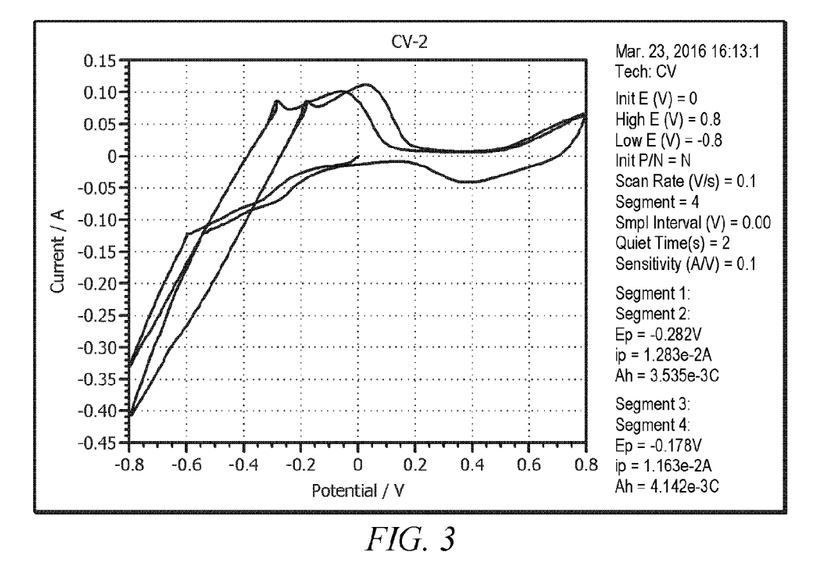
FIG. 3 illustrates a graphical representation of a second set of readings generated by a CV scan of the electrochemical sensor according to an embodiment.

A second CV scan (CV-2) may be completed with scan rate 0.1 V/s for about one minute with the same settings as the first CV scan (CV-1). The CV scan curve for CV-2 can be seen in FIG. 3. After the ethanol purging, the Pt—O curve peak has moved to approximately 0.38 V, which is approximately 0.78 V higher than the Pt—O curve peak of the CV-1 scan before the ethanol purging. The movement of the Pt—O reduction peak indicates that the sensor may be polluted.

Figure 4:
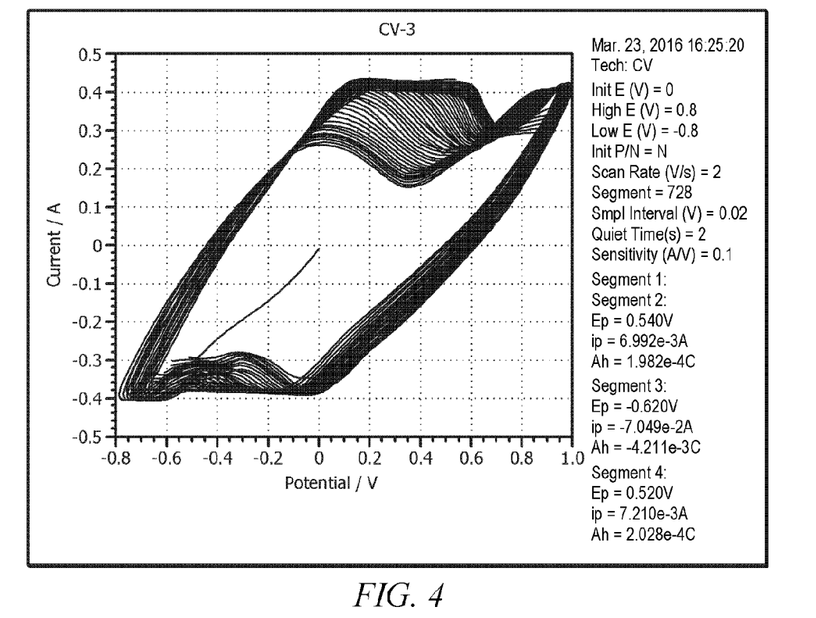
FIG. 4 illustrates a graphical representation of a third set of readings generated by a CV scan of the electrochemical sensor according to an embodiment.
Figure 5:
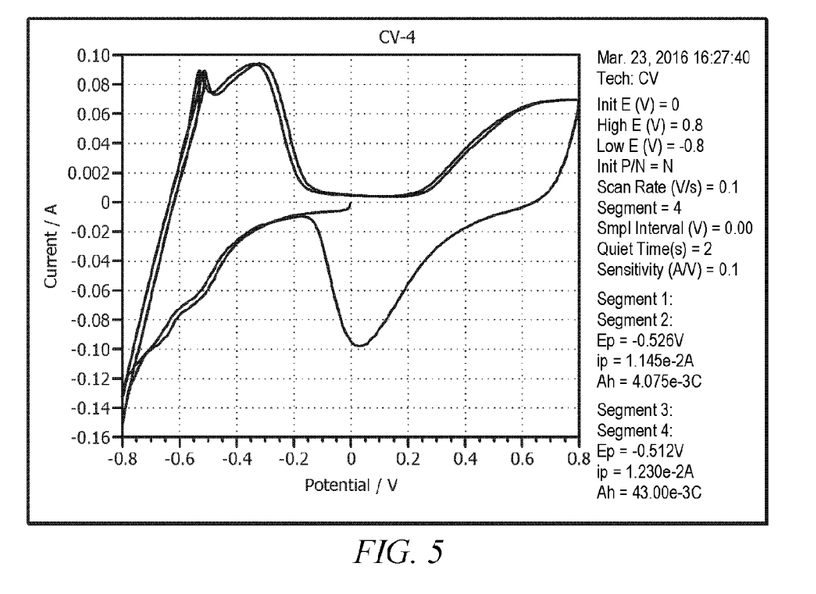
FIG. 5 illustrates a graphical representation of a fourth set of readings generated by a CV scan of the electrochemical sensor according to an embodiment.

Due to this diagnosis, rapid CV cleaning (CV-3) may be completed on the sensor (i.e. the reference electrode) with a rate of approximately 2 V/s for approximately 10 minutes. The set of readings generated by this cleaning is shown in FIG. 4. After the sensor has been cleaned using CV, yet another CV scan may be completed on the sensor to determine if the Pt—O reduction peak has been affected by the cleaning. So, a fourth CV scan (CV-4) may be completed on the sensor with a scan rate of approximately 0.1 V/s with the same settings as the CV-1 scan. The curve generated by CV-4 can be seen in FIG. 5. As shown in FIG. 5, the Pt—O reduction peak has moved to approximately 0.03 V, which is approximately 0.32 V lower when compared with the CV-2 scan (after the ethanol purge). Therefore, it can be seen that after cleaning (CV-3), the sensor Pt—O reduction curve moves closer to the CV-1 curve before ethanol purging, which may be considered a reference point and/or standard. A summary of the changes in the Pt—O reduction peak before and after ethanol purging, and before and after CV cleaning, can be seen in Table 1. The changes in the Pt—O reduction peak may indicate that the sensor is polluted and can be cleaned using the rapid CV scan.

TABLE 1

Pt—O Reduction Peak Before and After Ethanol Purging

| Example | Before ethanol purge | After ethanol purge | |
|---|---|---|---|
|  |  | CV scan with 0.1 V/s just after ethanol purge | CV scan with 0.1 V/s after rapid CV cleaning |
| Pt—O reduction curve peak (Volts) | −0.4 | 0.38 | 0.03 |

After the sensor has been cleaned using the rapid CV scanning, the sensor may be allowed to "rest" and return to a normal state. This may be accomplished by placing the sensor on an aging board and/or by allowing the sensor to remain in a charging state after the cleaning. In some embodiments, the sensor baseline may return to the normal state within approximately two hours, where the sensor may be employed after it has returned to normal.

Figure 6:
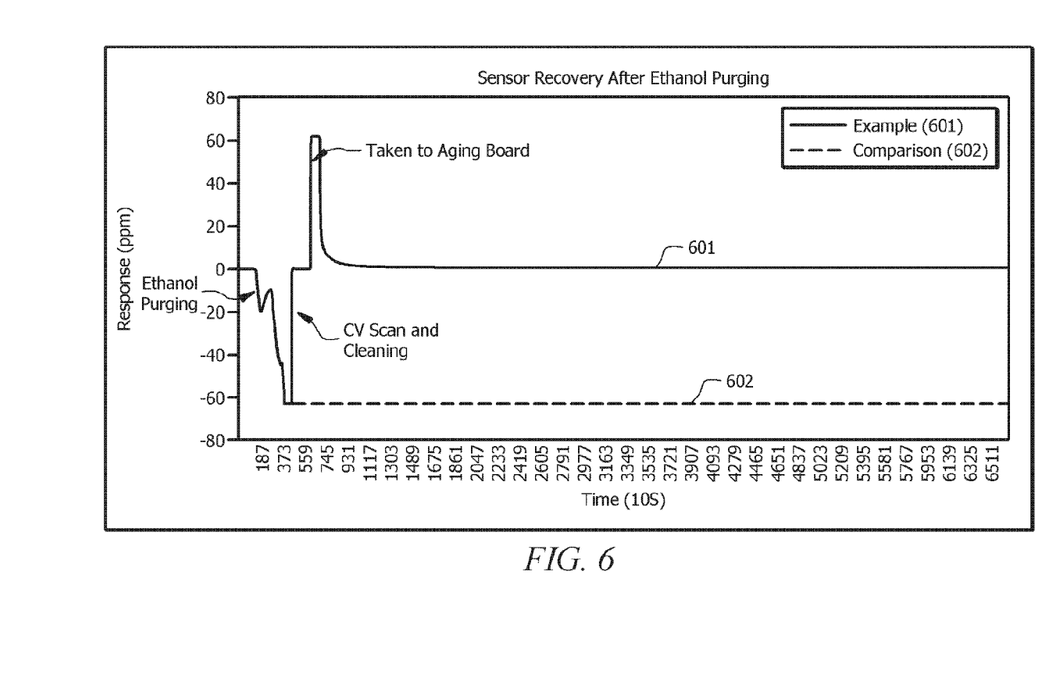
FIG. 6 illustrates a graphical representation of the response of the electrochemical sensor when cleaned, compared to the response of the electrochemical sensor when not cleaned, according to an embodiment.

FIG. 6 is a set of readings illustrating the response of the example sensor 601 described above and a comparison sensor 602. The comparison sensor 602 may be similar in configuration to the example sensor 601. Both sensors show negative responses quickly after the ethanol purging, and the sensors gradually reach approximately −62 ppm $H_2S$ near the limit of sensor board testing. The comparison sensor 602 does not undergo cleaning or CV scanning, and therefore the reading from the comparison sensor 602 remains near the limit of the sensor board reading. The comparison sensor 602 does not return to normal within the normal charging time for a sensor (approximately 16 hours), and therefore would not function correctly without a cleaning treatment.

However, between approximately an hour (3600 seconds) and 1.5 hours (5400 seconds), the example sensor 601 may be cleaned using the CV cleaning treatment as described above. This may cause the sensor reading to spike to a very high number due to the CV scanning, and after the CV scanning is complete, the sensor may be taken to an aging board where the sensor may be allowed to return to its normal operating state, for example, indicating a reading of 0 ppm. However, the example sensor 601 may be taken off the aging board to be cleaned using the CV scanning for about 13 minutes, as described above, and after the CV scanning is complete, the sensor may be taken to an aging board again. This may cause the sensor reading to spike to a very high number initially for about 10 minutes, due to the CV scanning, where the sensor may gradually return to its normal operating state after approximately 2 hours, for example indicating a reading of 0 ppm.

Figure 7:
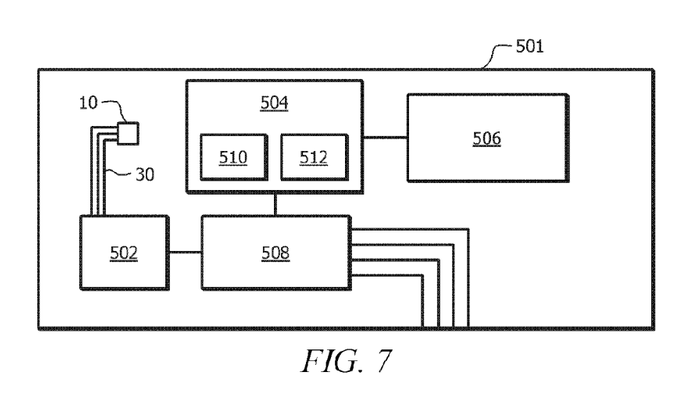
FIG. 7 schematically illustrates a sensor on a circuit board according to an embodiment.

FIG. 7 illustrates the sensor 10 in the context of a larger circuit. The circuit can include a circuit board 501, which can comprise a separate component from the sensor, a portion of the housing, or in some embodiments, an extension of the substrate such that the sensor 10 is formed on a single substrate that the other components are also disposed on. In this embodiment, the leads 30 may extend through a wall of the housing, and contact various external circuitry such as various sensing circuitry 506 (e.g. sensors, meters, etc.), a potentiostat 502, operating and control circuitry 504, communication circuitry 508, and the like. The sensor and meters can comprise additional sensors such as temperature and/or pressure sensors, which may allow for compensation of the sensor 10 outputs such that the compensation measurements are taken at or near the sensor 10 itself. Further, the location of the sensing circuitry 506 at or near the sensor 10 may allow smaller currents to be detected without intervening resistance, current loss, or electrical noise in longer electrical conductors. The control circuitry 504 may comprise a processor 510 and a memory 512 for performing various calculations and control functions, which can be performed in software or hardware. The communication circuitry 508 may allow the overall sensor results or readings to be communicated to an external source, and can include both wired communications using, for example, contacts on the board, or wireless communications using a transceiver operating under a variety of communication protocols (e.g., WiFi, Bluetooth, etc.). In some embodiments, the sensor 10 can be a separate component that is electrically coupled to external operating circuitry.

The control circuitry 504 of the sensor 10 may be operable to control the potentiostat 502 to complete the CV scans of the sensor. The control circuitry 504 may also receive the readings from the sensor 10 that are generated during the CV scans, and may be configured to analyze the readings, as described above.

Having described the devices and methods herein, various embodiments can include, but are not limited to:

In a first embodiment, a method for identifying contamination of an electrochemical sensor comprises scanning the electrochemical sensor a first time using CV before the electrochemical sensor has been employed; generating a reference set of readings from the first CV scan; scanning the electrochemical sensor a second time, using a similar scan to the first CV scan, after the electrochemical sensor has been employed; comparing a second set of readings from the second CV scan to the reference set of readings; when the second set of readings is different from the reference set of readings, determining that the electrochemical sensor potential has shifted; scanning the electrochemical sensor a third time, at a different rate from the first CV scan, to at least partially clean one or more elements of the electrochemical sensor; scanning the electrochemical sensor a fourth time, using a similar scan to the first CV scan; comparing a fourth set of readings from the fourth CV scan to the second set of readings; and when the fourth set of readings is different from the second set of readings and closer to the reference set of readings, determining that the potential of the electrochemical sensor has shifted due to pollution of the electrochemical sensor.

A second embodiment can include the method of the first embodiment, further comprising scanning the electrochemical sensor a fifth time, at the same rate as the third CV scan, to further clean the electrochemical sensor; and allowing the electrochemical sensor to return to a normal operating state before the electrochemical sensor is employed.

A third embodiment can include the method of the first or second embodiments, wherein determining that the electrochemical sensor potential has shifted comprises determining that the potential of a reference electrode of the electrochemical sensor has shifted.

A fourth embodiment can include the method of the third embodiment, wherein scanning the electrochemical sensor a third time to clean the electrochemical sensor comprises scanning the reference electrode to clean the reference electrode.

A fifth embodiment can include the method of the third or fourth embodiments, wherein determining that the potential of the electrochemical sensor has shifted due to pollution of the electrochemical sensor comprises determining that the potential of the reference electrode has shifted due to pollution of the reference electrode.

A sixth embodiment can include the method of any of the first to fifth embodiments, wherein the scanning is completed by a control circuitry of the electrochemical sensor.

A seventh embodiment can include the method of any of the first to sixth embodiments, wherein the scan rate for the third scanning is between approximately 0.5 to 5 Volts per second (V/s).

An eighth embodiment can include the method of any of the first to seventh embodiments, wherein the range for the third scanning is from approximately −0.8 to 0.8 Volts.

A ninth embodiment can include the method of any of the first to eighth embodiments, wherein the time of scanning for the third scan is between approximately 12 minutes and 48 minutes.

A tenth embodiment can include the method of any of the first to ninth embodiments, wherein comparing the second set of readings with the reference set of readings comprises observing one or more peaks indicating hydrogen adsorption.

An eleventh embodiment can include the method of any of the first to tenth embodiments, wherein comparing the second set of readings with the reference set of readings comprises observing one or more peaks indicating oxygen reduction.

A twelfth embodiment can include the method of any of the first to eleventh embodiments, wherein the contamination of the electrochemical sensor comprises one or more of a VOC gas, a high concentration of test gases, or interfering gases.

A thirteenth embodiment can include the method of the twelfth embodiment, wherein the contamination of the electrochemical sensor comprises a pollutant generated within the electrochemical sensor, such as one or more of the sensor housing, electrolyte, catalyst, epoxy, contact wires, or assembly material for the electrochemical sensor.

In a fourteenth embodiment, an electrochemical sensor comprises a housing; an electrolyte disposed within the housing; and a plurality of electrodes in contact with the electrolyte within the housing, wherein the plurality of electrodes comprises a working electrode and a counter electrode; a control circuitry configured to scan the electrochemical sensor a first time using CV before the electrochemical sensor has been employed, thereby generating a reference set of readings from the first CV scan; scan the electrochemical sensor a second time, using a similar scan to the first CV scan, after the electrochemical sensor has been employed, wherein a second set of readings from the second CV scan is compared to the to the reference set of readings; when the second set of readings is different from the reference set of readings, scan the electrochemical sensor a third time, at a different rate from the first CV scan, to at least partially clean one or more elements of the electrochemical sensor; scan the electrochemical sensor a fourth time, using a similar scan to the first CV scan, wherein a fourth set of readings from the fourth CV scan is compared to the second set of readings; and when the fourth set of readings is different from the second set of readings and closer to the reference set of readings, determine that the potential of the electrochemical sensor has shifted due to pollution of the electrochemical sensor.

A fifteenth embodiment can include the electrochemical sensor of the fourteenth embodiment, wherein the control circuitry is further configured to scan the electrochemical sensor a fifth time, at the same rate as the third CV scan, to further clean the electrochemical sensor, wherein the electrochemical sensor is then allowed to return to a normal operating state before the electrochemical sensor is employed.

A sixteenth embodiment can include the electrochemical sensor of the fourteenth or fifteenth embodiments, further comprising a reference electrode, wherein the contamination of the electrochemical sensor comprises contamination of the reference electrode.

A seventeenth embodiment can include the electrochemical sensor of the sixteenth embodiment, wherein the third CV scan to clean the electrochemical sensor comprises a scan of the reference electrode to clean the reference electrode.

An eighteenth embodiment can include the electrochemical sensor of any of the fourteenth to seventeenth embodiments, wherein the scan rate for the third scan is between approximately 0.5 to 5 Volts per second (V/s).

A nineteenth embodiment can include the electrochemical sensor of any of the fourteenth to eighteenth embodiments, wherein the range for the third scan is from approximately −0.8 to 0.8 Volts.

A twentieth embodiment can include the electrochemical sensor of any of the fourteenth to nineteenth embodiments, wherein the time of scanning for the third scan is between approximately 12 minutes and 48 minutes.

In a twenty-first embodiment, a method for identifying contamination of an electrochemical sensor may comprise scanning the electrochemical sensor a first time using CV before the electrochemical sensor has been employed; generating a reference set of readings from the first CV scan; scanning the electrochemical sensor a second time, using a similar scan to the first CV scan, after the electrochemical sensor has been employed; comparing a second set of readings from the second CV scan to the reference set of readings; when the second set of readings is different from the reference set of readings, determining that the electrochemical sensor potential has shifted; scanning the electrochemical sensor a third time, at a different rate from the first CV scan, to at least partially clean one or more elements of the electrochemical sensor; scanning the electrochemical sensor a fourth time, using a similar scan to the first CV scan; comparing a fourth set of readings from the fourth CV scan to the second set of readings; and determining at least one of: that the potential of the electrochemical sensor has shifted due to pollution of the electrochemical sensor, or that the electrochemical sensor can be further cleaned.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification, and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as "comprises," "includes," and "having" should be understood to provide support for narrower terms such as "consisting of," "consisting essentially of," and "comprised substantially of." Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system, or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A method for identifying contamination of an electrochemical sensor, the method comprising:
   scanning the electrochemical sensor a first time using cyclic voltammetry (CV) in a first CV scan before the electrochemical sensor has been employed;
   generating a reference set of readings from the first CV scan;
   scanning the electrochemical sensor a second time in a second CV scan, using a similar scan to the first CV scan, after the electrochemical sensor has been employed;
   comparing a second set of readings from the second CV scan to the reference set of readings;
   when the second set of readings is different from the reference set of readings, determining that an electrochemical sensor potential has shifted indicating hydrogen adsorption and/or oxygen reduction;
   scanning the electrochemical sensor a third time in a third CV scan, at a different rate from the first CV scan, to at least partially clean one or more elements of the electrochemical sensor;
   scanning the electrochemical sensor a fourth time in a fourth CV scan, using a similar scan to the first CV scan;
   comparing a fourth set of readings from the fourth CV scan to the second set of readings; and
   when the fourth set of readings is different from the second set of readings and closer to the reference set of readings, determining that the electrochemical sensor potential of the electrochemical sensor had shifted due to pollution of the electrochemical sensor.

2. The method of claim 1, further comprising:
   scanning the electrochemical sensor a fifth time, at the same rate as the third CV scan, to further clean the electrochemical sensor; and
   allowing the electrochemical sensor to return to a normal operating state before the electrochemical sensor is employed.

3. The method of claim 1, wherein determining that the electrochemical sensor potential has shifted comprises determining that the electrochemical sensor potential of a reference electrode of the electrochemical sensor has shifted.

4. The method of claim 3, wherein scanning the electrochemical sensor the third time to clean the electrochemical sensor comprises scanning the reference electrode to clean the reference electrode.

5. The method of claim 3, wherein determining that the electrochemical sensor potential of the electrochemical sensor has shifted due to pollution of the electrochemical sensor comprises determining that the electrochemical sensor potential of the reference electrode has shifted due to the pollution of the reference electrode.

6. The method of claim 1, wherein the scanning is completed by a control circuitry of the electrochemical sensor.

7. The method of claim 1, wherein the rate for the third CV scan is between approximately 0.5 to 5 Volts per second (V/s).

8. The method of claim 1, wherein a range for the third CV scan is from approximately −0.8 to 0.8 Volts.

9. The method of claim 1, wherein time of scanning for the third scan is between approximately 12 minutes and 48 minutes.

10. The method of claim 1, wherein the contamination of the electrochemical sensor comprises one or more of a VOC gas, a high concentration of a test gases, an interfering gases, or a pollutant generated within the electrochemical sensor, from one or more of a housing, electrolyte, catalyst, epoxy, contact wires, or assembly material for the electrochemical sensor.

11. A sensor system comprising:
an electrochemical sensor comprising:
a housing;
an electrolyte disposed within the housing; and
a plurality of electrodes in contact with the electrolyte within the housing, wherein the plurality of electrodes comprise a working electrode, a counter electrode;
a control circuitry configured to:
scan the electrochemical sensor a first time using cyclic voltammetry (CV) in a first CV scan before the electrochemical sensor has been employed, thereby generating a reference set of readings from the first CV scan;
scan the electrochemical sensor a second time in a second CV scan, using a similar scan to the first CV scan, after the electrochemical sensor has been employed, wherein a second set of readings from the second CV scan is compared to the to the reference set of readings;
when the second set of readings is different from the reference set of readings, scan the electrochemical sensor a third time in a third CV scan, at a different rate from the first CV scan, to at least partially clean one or more elements of the electrochemical sensor;
scan the electrochemical sensor a fourth time in a fourth CV scan, using a similar scan to the first CV scan, wherein a fourth set of readings from the fourth CV scan is compared to the second set of readings; and
when the fourth set of readings is different from the second set of readings and closer to the reference set of readings, determine that the electrochemical sensor potential of the electrochemical sensor has shifted due to pollution of the electrochemical sensor.

12. The sensor system of claim 11, wherein the control circuitry is further configured to scan the electrochemical sensor a fifth time, at the same rate as the third CV scan, to further clean the electrochemical sensor, wherein the electrochemical sensor is then allowed to return to a normal operating state before the electrochemical sensor is employed.

13. The sensor system of claim 11, further comprising a reference electrode, wherein contamination of the electrochemical sensor comprises contamination of the reference electrode.

14. The sensor system of claim 13, wherein the third CV scan to clean the electrochemical sensor comprises a scan of the reference electrode to clean the reference electrode.

15. The sensor system of claim 11, wherein the rate for the third CV scan is between approximately 0.5 to 5 Volts per second (V/s).

16. The sensor system of claim 11, wherein a range for the third CV scan is from approximately −0.8 to 0.8 Volts.

17. The sensor system of claim 11, wherein time of scanning for the third scan is between approximately 12 minutes and 48 minutes.

18. A method for identifying contamination of an electrochemical sensor, the method comprising:
scanning the electrochemical sensor a first time using cyclic voltammetry (CV) in a first CV scan before the electrochemical sensor has been employed;
generating a reference set of readings from the first CV scan;
scanning the electrochemical sensor a second time in a second CV scan, using a similar scan to the first CV scan, after the electrochemical sensor has been employed;
comparing a second set of readings from the second CV scan to the reference set of readings;
when the second set of readings is different from the reference set of readings, determining that an electrochemical sensor potential has shifted indicating hydrogen adsorption or oxygen reduction;
scanning the electrochemical sensor a third time, at a different rate from the first CV scan, to at least partially clean one or more elements of the electrochemical sensor;
scanning the electrochemical sensor a fourth time in a fourth CV scan, using a similar scan to the first CV scan;
comparing a fourth set of readings from the fourth CV scan to the second set of readings; and
determining at least one of: that the electrochemical sensor potential of the electrochemical sensor has shifted due to pollution of the electrochemical sensor, or that the electrochemical sensor can be further cleaned.

* * * * *